United States Patent
Rezai et al.

(10) Patent No.: US 7,640,063 B2
(45) Date of Patent: Dec. 29, 2009

(54) METHODS OF TREATING MEDICAL CONDITIONS BY NEUROMODULATION OF THE CEREBELLAR PATHWAYS

(75) Inventors: Ali R. Rezai, Bratenhal, OH (US); Andre Machado, Sao Paulo SP (BR)

(73) Assignee: The Cleveland Clinic Foundation, Cleveland, OH (US)

( * ) Notice: Subject to any disclaimer, the term of this patent is extended or adjusted under 35 U.S.C. 154(b) by 485 days.

(21) Appl. No.: 11/121,005

(22) Filed: May 4, 2005

(65) Prior Publication Data

US 2005/0283200 A1 Dec. 22, 2005

Related U.S. Application Data

(60) Provisional application No. 60/567,441, filed on May 4, 2004, provisional application No. 60/608,419, filed on Sep. 10, 2004.

(51) Int. Cl.
*A61N 1/36* (2006.01)
(52) U.S. Cl. ........................................................ 607/45
(58) Field of Classification Search .................... 607/45
See application file for complete search history.

(56) References Cited

U.S. PATENT DOCUMENTS

| | | | | |
|---|---|---|---|---|
| 4,378,797 A | * | 4/1983 | Osterholm | 604/24 |
| 4,445,500 A | * | 5/1984 | Osterholm | 604/28 |
| 5,259,387 A | | 11/1993 | dePinto | |
| 5,711,316 A | | 1/1998 | Elsberry et al. | |
| 6,058,331 A | | 5/2000 | King | |
| 6,066,163 A | * | 5/2000 | John | 607/45 |
| 6,353,762 B1 | | 3/2002 | Baudino et al. | |
| 6,366,813 B1 | | 4/2002 | Dilorenzo | |
| 6,368,331 B1 | | 4/2002 | Front et al. | |
| 7,236,830 B2 | * | 6/2007 | Gliner | 607/45 |
| 2002/0032375 A1 | | 3/2002 | Bauch et al. | |
| 2002/0183607 A1 | | 12/2002 | Bauch et al. | |
| 2003/0149450 A1 | | 8/2003 | Mayberg | |
| 2004/0133248 A1 | * | 7/2004 | Frei et al. | 607/45 |
| 2004/0186532 A1 | * | 9/2004 | Tadlock | 607/48 |
| 2006/0004422 A1 | | 1/2006 | De Ridder | |
| 2006/0069415 A1 | | 3/2006 | Cameron et al. | |

* cited by examiner

*Primary Examiner*—Carl H Layno
*Assistant Examiner*—Brian T Gedeon
(74) *Attorney, Agent, or Firm*—Kenyon & Kenyon LLP

(57) ABSTRACT

Methods of treating various medical conditions by neuromodulation of target sites of a cerebello-thalamo-cortical pathway and/or a cortical-ponto-cerebellar pathway. Such medical conditions include unilateral motor deficits, movement disorders, psychiatric disorders, epilepsy, speech or cognitive deficits associated with hemispheric lesions, visual deficits associated with hemispheric lesions, learning disorders associated with hemispheric lesions, vertigo and/or dizziness, gait disturbances, hereditary/genetic disorders, congenital malformations, infectious disease, degenerative disorders, autoimmune disorders, and metabolic disorders. A method of enhancing memory, learning and/or cognitive capacity in a normal individual by stimulating a target site of a cerebello-thalamo-cortical pathway and/or a cortical-ponto-cerebellar pathway is also provided.

7 Claims, 3 Drawing Sheets

METHODS OF TREATING MEDICAL CONDITIONS BY NEUROMODULATION OF THE CEREBELLAR PATHWAYS

CROSS-REFERENCE TO RELATED APPLICATIONS

The present application claims priority to U.S. Provisional Application Nos. 60/567,441 filed on May 4, 2004 and 60/608,419 filed on Sep. 10, 2004, both of which are incorporated by reference herein.

FIELD OF THE INVENTION

The present invention relates to systems and methods of treating medical conditions by electrical and/or chemical neuromodulation of target sites of the cerebello-thalamo-cortical pathway and the cortical-ponto-cerebellar pathway.

BACKGROUND OF THE INVENTION

Electrical stimulation of neural tissue is becoming an increasingly preferred form of therapy for certain neurological conditions and disorders where existing therapies generate intolerable side effects, require repeated administration of treatment, or are simply ineffective in a subset of patients. Electrical stimulation provides distinct advantages over surgical lesioning techniques since electrical stimulation is a reversible and adjustable procedure that provides continuous benefits as the patient's disease progresses and the patient's symptoms evolve.

Currently, electrical stimulation of peripheral nerves and the spinal cord is approved for treatment of neuropathic pain. With respect to deep brain targets, electrical stimulation of the subthalamic nucleus and the globus pallidus interna is approved for treatment of Parkinson's disease and electrical stimulation of the ventral intermediate nucleus is approved for treatment of essential tremor.

There remains a need for further forms of neuromodulation to treat these and other disorders.

SUMMARY OF THE INVENTION

In an embodiment, the present invention provides a system for treating a medical condition comprising a therapy delivery device for positioning on a target site of a cerebello-thalamo-cortical pathway and/or a cortical-ponto-cerebellar pathway and a controller in communication with the therapy delivery device for enabling the therapy delivery device to deliver therapy to the target site to treat the medical condition. The therapy delivery device can be a stimulation lead for delivering electrical neuromodulation or a drug port for delivering chemical neuromodulation to the target site.

The present invention also provides a system for treating a medical condition comprising a therapy delivery device for applying a therapy signal on a target site of a cerebello-thalamo-cortical pathway and/or a cortical-ponto-cerebellar pathway. The system also include a sensor for detecting a bodily activity associated with the medical condition and for generating a sensor signal. The system also includes a controller in communication with the therapy delivery device and the sensor for activating the therapy delivery device to initiate application of the therapy signal to the target site or to adjust application of the therapy signal to the target site in response to the sensor signal. The therapy signal can be an electrical signal in embodiments where the therapy delivery device is a stimulation lead and a chemical signal in embodiments where the therapy delivery device is a drug port.

The present invention also provides a method for treating a medical condition comprising placing a therapy delivery device on a target site of a cerebello-thalamo-cortical pathway and/or a cortical-ponto-cerebellar pathway and activating the therapy delivery device to deliver therapy to the target site to treat the medical condition condition.

The present invention moreover provides a method of enhancing memory, learning and/or cognitive capacity in a normal individual by neuromodulation of a target site of a cerebello-thalamo-cortical pathway and/or a cortical-ponto-cerebellar pathway.

DETAILED DESCRIPTION OF THE INVENTION

Figure 1:
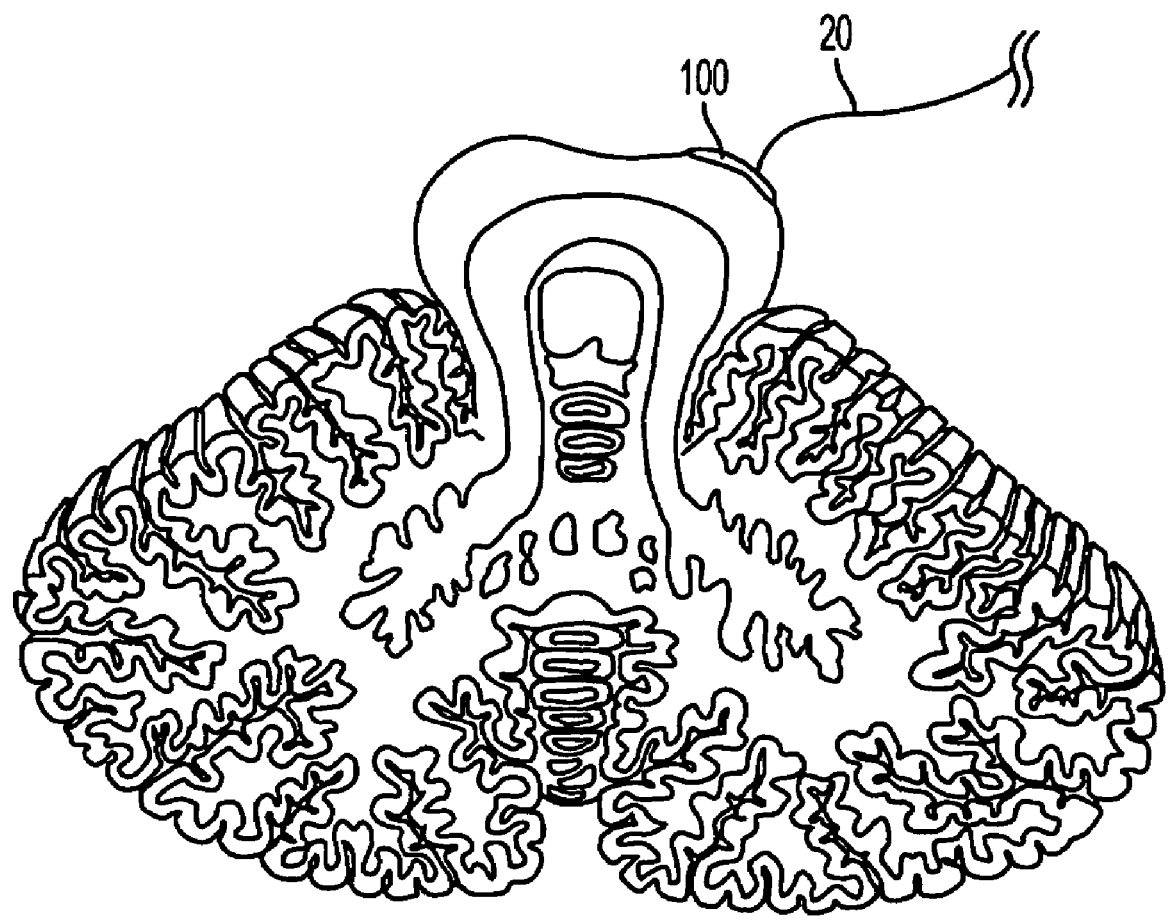
FIG. 1 is a therapy delivery device positioned at a target site of a cerebello-thalamo-cortical pathway and/or a cortical-ponto-cerebellar pathway.

The present invention provides systems and methods for treating medical conditions by neuromodulating a cerebello-thalamo-cortical pathway and/or a cortical-ponto-cerebellar pathway. The cerebello-thalamo-cortical pathway is neural circuitry from the cerebellum to the motor thalamus to the cerebral cortex. The cortical-ponto-cerebellar pathway is the pathway from the cerebral cortex to the pons back to the cerebellum. Therefore the cerebello-thalamo-cortical pathway and the cortical-ponto-cerebellar pathway form a loop to and from the cerebellum. Non-limiting examples of target sites within these pathways include deep cerebellar target sites within the cerebellum (i.e. not on the cerebellar cortex). Deep cerebellar target sites include the cerebellar nuclei, the white matter around the nuclei, and the cerebellar peduncles. Cerebellar nuclei include the fastigial nuclei, the interposed (including the inferior globuse and emboliform) nuclei, and dentate nuclei. The cerebellar peduncles include the inferior cerebellar peduncle, the middle cerebellar peduncle, and the superior cerebellar peduncle. The systems and methods of the present invention for treating medical conditions encompass neuromodulation of any combination of one or more target sites of the cerebello-thalamo-cortical pathway and/or cortical-ponto-cerebellar pathway. The present invention also encompasses systems and methods for treating medical conditions by neuromodulating a red nucleus.

As used herein, the term "treating" a medical condition encompasses therapeutically regulating, preventing, improving, alleviating the symptoms of, reducing the effects of and/or diagnosing the medical condition. As used herein, the term "medical condition" encompasses any condition, disease, disorder, function, abnormality, or deficit that is affected by neuromodulation of the cerebello-thalamo-cortical pathway and/or cortical-ponto-cerebellar pathway. Non-limiting examples of medical conditions that can be treated according to the present invention include language deficits, visual deficits, motor deficits, cognitive deficits, learning deficits, sensory deficits, psychiatric disorders, movement disorders, pain syndromes, stroke, autism, vertigo, dizziness, hereditary/genetic disorders, a congenital malformation, an infectious disease, a degenerative disorder, an autoimmune disorder, or a metabolic disorder. Further, the medical condition can be the result of any etiology including vascular, ischemic including stroke, thrombotic, embolic, infectious (including bacterial, viral, parasitic, fungal, abscessal), neoplastic, drug-induced, metabolic, immunological, inflammatory, collagenic, traumatic, surgical, chemotherapeutic, radiation, idiopathic, endocrinological, allergic, degenerative, congenital, or abnormal malformational causes.

Non-limiting examples of motor deficits include lack of coordination, gait disturbance, paralysis, hemiparesis, or paresis. Non-limiting examples of visual deficits include blindness. Non-limiting examples of cognitive deficits include aphasia and apraxia. A non-limiting example of a sensory deficit is hypoesthesia. Non-limiting examples of psychiatric disorders are addiction/substance abuse, obsessive compulsive disorder, generalized anxiety disorder, post traumatic stress disorder, panic attacks, social phobia, depression, bipolar disorder and other mood disorders, and schizophrenia. Non-limiting examples of movement disorders include Parkinson's disease, essential tremor, spasticity, rigidity, bradykinesia, post-traumatic movement disorder, post-ischemic and post-injury movement disorder. Non-limiting examples of pain syndromes include migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

In a preferred embodiment, the medical condition is cognitive function, depression or other mood disorders, learning and learning disorders, or motor learning.

FIG. 1 provides an illustration of a therapy delivery device 100, according to an embodiment of the present invention positioned at a target site of a cerebello-thalamo-cortical pathway and/or a cortical-ponto-cerebellar pathway system (which in this exemplary illustration is a cerebellar peduncle). Therapy delivery device is connected via a stimulation lead/catheter 20 (in embodiments where therapy delivery device is a stimulation lead and drug port respectively) for connection to a controller (not shown). The therapy delivery device has a configuration that allows the therapy deliver device to maximize contact with and optimally deliver therapy to the target site.

In embodiments where the therapy delivery device is a stimulation lead having a lead proximal end, a lead body, and a lead distal end, the lead distal end comprises at least one electrode. The at least one electrode can be a plurality of electrodes. The electrodes at the lead distal end can be either monopolar, bipolar, or multipolar, and can operate as a cathode or an anode. The electrode can be composed of but not limited to activated iridium, rhodium, titanium, or platinum and combinations of said materials. The electrode may be coated with a thin surface layer of iridium oxide, titanium nitride or other surface modifications to enhance electrical sensitivity. The stimulation lead can also comprise carbon, doped silicon, or silicon nitride. Each lead distal end can be provided with a biocompatible fabric "collar" or band about the electrode periphery to allow it to be more readily sutured or glued into place (for electrodes to be secured in this manner). The stimulation lead may be placed permanently or temporarily in the target site to provide chronic or acute neuromodulation of the target site.

The controller is used to operate and supply power to the therapeutic delivery device and enable the therapy delivery device to delivery a therapy signal (such as an electrical signal or a chemical signal) to the target site. The controller may be powered by a battery (which may be rechargeable), an external power supply, a fuel cell, or a battery pack for external use. The controller may also be integral with the therapeutic delivery device (such as a single stimulation lead/power generator). When the therapeutic delivery device is a stimulation lead, the controller may change the output to the electrode by way of polarity, pulse width, amplitude, frequency, voltage, current, intensity, duration, wavelength, and/or waveform. When the therapeutic delivery device is a drug port, the controller may change its output such that a pump, pressure source, or proportionally controlled orifice increases or decreases the rate at which the pharmaceutical is delivered to the target site. The controller may operate any number or combination of electrodes, and pharmaceutical delivery devices, for example the controller may be connected to stimulation leads and a peristaltic pump for delivering a pharmaceutical to the target site near the stimulation leads. The controller may be implanted within the patient or it may be positioned by leads outside of the patient. A portion of the control system may be external to the patient's body for use by the attending physician to program the implanted controller and to monitor its performance. This external portion may include a programming wand which communicates with the implanted controller by means of telemetry via an internal antenna to transmit parameter values (as may be selectively changed from time to time by subsequent programming) selected at the programmer unit, such as a computer. The programming wand also accepts telemetry data from the controller to monitor the performance of the therapy delivery device.

In embodiments where the controller enables a stimulation lead to deliver an electrical signal to the target site, the electrical signal may be episodic, continuous, phasic, in clusters, intermittent, upon demand by the patient or medical personnel, or preprogrammed to respond to a sensor. Preferably, the oscillating electrical signal is operated at a voltage between about 0.1 microvolts to about 20 V. More preferably, the oscillating electrical signal is operated at a voltage between about 1 V to about 15 V. For microstimulation, it is preferable to stimulate within the range of 0.1 microvolts to about 1 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the stimulation lead is monopolar; bipolar when the stimulation lead is bipolar; and multipolar when the stimulation lead is multipolar. The waveform may be, for example, biphasic, square wave, sine wave, or other electrically safe and feasible combinations. The electrical signal may be applied to multiple target sites simultaneously or sequentially.

In embodiments where the controller enables a drug port to deliver a chemical signal to the target site, a chemical agent may be delivered to the target site prior to, concurrent with, subsequent to or instead of electrical neuromodulation. The chemical agent may be a neurotransmitter mimick; neuropeptide; hormone; pro-hormone; antagonist, agonist, reuptake inhibitor, or degrading enzyme thereof; peptide; protein; therapeutic agent; amino acid; nucleic acid; stem cell or any combination thereof and may be delivered by a slow release matrix or drug pump. The delivery of the chemical agent may be continuous, intermittent, chronic, phasic, or episodic. Different chemical agents may be utilized to affect different parts of the sympathetic nervous system. The chemical agents preferably work on one or more of the receptor sites of the autonomic nervous system such as the adrenergic receptors, cholinergic receptors (nicotinic and muscarinic), purinergic, and nitric oxide receptors. Non-limiting examples of chemical agents include, prazosin, yohimbine, atelenol, sulbutamol, and atropine.

The present invention also provides systems for treating medical conditions incorporating a closed-loop feedback mechanism. Specifically, in such embodiments, the system comprises a therapy delivery device for applying a therapy signal (which can be an electrical signal or a chemical signal) on a target site of the cerebello-thalamo-cortical pathway and/or a cortical-ponto-cerebellar pathway. The system further comprises a sensor for detecting a bodily activity associated with the medical condition and for generating a sensor signal. The system also includes a controller in communication with the therapy delivery device for activating the therapy delivery device to initiate application of the therapy signal to the target site or to adjust application of the therapy signal to the target site in response to the sensor signal. The bodily activity to be detected by the sensor is any characteristic or function of the body, such as electrical or chemical activity and includes, for example, temperature, respiratory function, heart rate, capillary pressure, venous pressure, perfusion, oxygenation including blood oxygenation levels, oxygen saturation levels, oxygen consumption, oxygen pressure, water pressure, nitrogen pressure, carbon dioxide pressure in the tissue, circulation (including blood and lymphatic), electrolyte levels in the circulation/tissue, diffusion or metabolism of various agents and molecules (such as glucose), neurotransmitter levels, body temperature regulation, blood pressure, blood viscosity, metabolic activity, cerebral blood flow, pH levels, vital signs, galvanic skin responses, perspiration, electrocardiogram, electroencephalogram, action potential conduction, chemical production, body movement, response to external stimulation, cognitive activity, motor activity including muscle tone, visual activity, speech, balance, diaphragmatic movement, chest wall expansion, concentration of certain biological molecules/substances in the body such as, for example, glucose, liver enzymes, electrolytes, hormones, creatinine, medications, concentration of various cells, platelets, or bacteria. These bodily activities can be measured utilizing a variety of methods including but not limited to chemical analysis, mechanical measurements, laser, and fiber-optic analysis.

In specific embodiments, the sensors are located on or within the body and detect electrical and/or chemical activity. Such activity may be detected by sensors located within or proximal to the target site, distal to the target site but within the nervous system, or by sensors located distal to the target site outside the nervous system. Examples of electrical activity detected by sensors located within or proximal to the target site include sensors that measure neuronal electrical activity, such as the electrical activity characteristic of the signaling stages of neurons (i.e. synaptic potentials, trigger actions, action potentials, and neurotransmitter release) at the target site and by afferent and efferent pathways and sources that project to and from or communicate with the target site. For example, the sensors can measure, at any signaling stage, neuronal activity of any of the extensive connections of the target site. In particular, the sensors may detect the rate and pattern of the neuronal electrical activity to determine the electrical signal to be provided to the lead.

Examples of chemical activity detected by sensors located within or proximal to the target site include sensors that measure neuronal activity, such as the modulation of neurotransmitters, hormones, pro-hormones, neuropeptides, peptides, proteins, electrolytes, or small molecules by the target site and modulation of these substances by afferent and efferent pathways and sources that project to and from the target sites or communicate with the target sites.

With respect to detecting electrical or chemical activity of the body by sensors located distal to the target site but still within the nervous system, such sensors could be placed in the brain, the spinal cord, cranial nerves, and/or spinal nerves. Sensors placed in the brain are preferably placed in a layerwise manner in the direction of increasing proximity to the target site. For example, a sensor could be placed on the scalp (i.e. electroencephalogram), in the subgaleal layer, on the skull, in the dura mater, in the sub dural layer and in the parenchyma (i.e. in the frontal lobe, occipital lobe, parietal lobe, temporal lobe) to achieve increasing specificity of electrical and chemical activity detection. The sensors could measure the same types of chemical and electrical activity as the sensors placed within or proximal to the target site as described above.

With respect to detecting electrical or chemical activity by sensors located distal to the target site outside the nervous system, such sensors may be placed in venous structures and various organs or tissues of other body systems, such as the endocrine system, muscular system, respiratory system, circulatory system, urinary system, integumentary system, and digestive system or such sensors may detect signals from these various body systems. For example, the sensor may be an external sensor such as a pulse oximeter, or an external blood pressure, heart, and respiratory rate detector. All the above-mentioned sensing systems may be employed together or any combination of less than all sensors may be employed together.

After the sensor(s) detect the relevant bodily activity associated with the medical condition, according to the systems of the present invention, the sensors generate a sensor signal. The sensor signal is processed by a sensor signal processor, which in this embodiment is part of the controller. The controller generates a response to the sensor signal by activating the therapy delivery device to initiate application of the therapy signal or to adjust application of the therapy signal to the target site. The therapy deliver device then applies the therapy signal to the target site. In embodiments where the therapy delivery device is a stimulation lead and the therapy signal is an electrical signal, activating the stimulation lead to adjust application of the electrical signal includes terminating, increasing, decreasing or changing the rate or pattern of a pulsing parameter of the electrical stimulation and the electrical signal can be the respective termination, increase, decrease or change in rate or pattern of the respective pulsing parameter. In embodiments where the therapy delivery device is a drug port and the therapy signal is a chemical signal, activating the drug port to adjust application of the chemical signal can be an indication to terminate, increase, decrease or change the rate or pattern of the amount or type of chemical agent administered, and the chemical signal can be the respective initiation, termination, increase, decrease or change in the rate or pattern of the amount or type of chemical agent administered. The processing of closed-loop feedback systems for electrical and chemical stimulation are described in more detail in respective U.S. Pat. Nos. 6,058,331 and 5,711,316, both of which are incorporated by reference herein.

Figure 2:
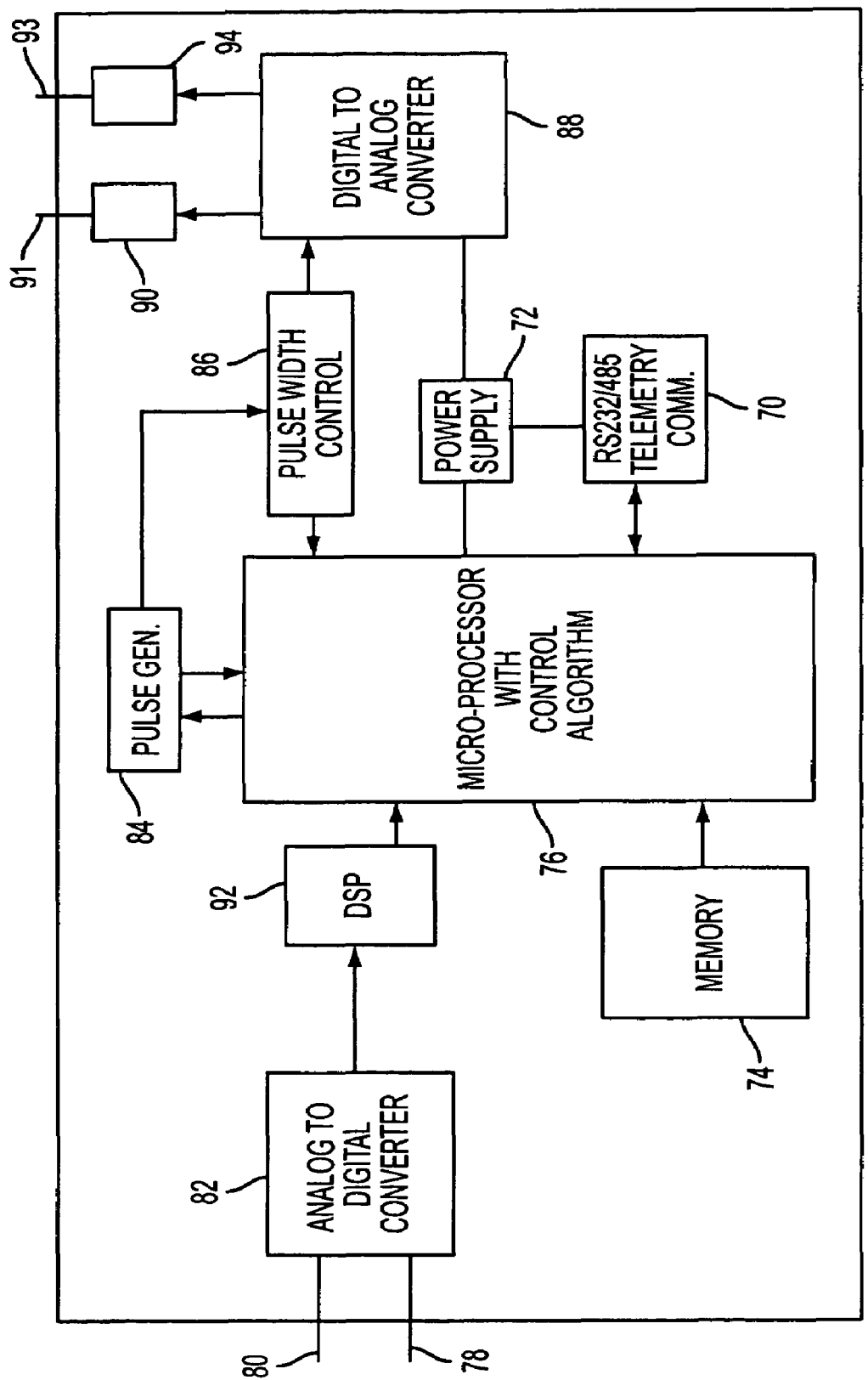
FIG. 2 is a schematic illustration of the components which may be used in a controller of the present invention.

Closed-loop electrical stimulation, according to the present invention can be achieved by a modified form of an implantable SOLETRA, KINETRA, RESTORE, or SYNERGY signal generator available from Medtronic, Minneapolis, Minn. as disclosed in U.S. Pat. No. 6,353,762, the teaching of which is incorporated herein in its entirety, a controller as described in FIG. 2, or utilization of CIO DAS 08 and CIO-DAC 16 I processing boards and an IBM compatible computer available from Measurement Computing, Middleboro, Mass. with Visual Basic software for programming of alogorithms. With reference to FIG. 2 an illustration of a non-limiting example of a controller comprising a microprocessor 76 such as an MSP430 microprocessor from Texas Instruments Technology, analog to digital converter 82 such as AD7714 from Analog Devices Corp., pulse generator 84 such as CD1877 from Harris Corporation, pulse width control 86, lead driver 90, digital to analog converter 88 such as MAX538 from Maxim Corporation, power supply 72, memory 74, and communications port or telemetry chip 70 are shown. Optionally, a digital signal processor 92 is used for signal conditioning and filtering. Input leads 78 and 80 and output lead to lead (therapeutic delivery device) 91 and drug delivery device (therapeutic deliver device) 93 are also illustrated. Additional stimulation leads, sensors, and therapeutic delivery devices may be added to the controller as required. As a non-limiting example, inputs from sensors, such as heart rate and blood pressure sensors, are input to analog to digital converter 82. Microprocessor 76 receiving the sensor inputs uses algorithms to analyze the biological activity of the patient and using PID, Fuzzy logic, or other algorithms, computes an output to pulse generator and/or drug delivery device drivers 90 and 94, respectively, to neuromodulate the target site where the therapeutic delivery devices are placed. The output of analog to digital converter 82 is connected to microprocessor 76 through a peripheral bus including address, data and control lines. Microprocessor 76 processes the sensor data in different ways depending on the type of transducer in use. When the signal on the sensor indicates biological activity outside of threshold values, for example elevated blood pressure or heart rate, programmed by the clinician and stored in a memory, the electrical signal applied through output drivers 90 and 94 of the controller will be adjusted. The output voltage or current from the controller are then generated in an appropriately configured form (voltage, current, frequency), and applied to the one or, more therapeutic delivery devices placed at the target site for a prescribed time period to reduce elevated blood pressure or heart rate. If the patient's blood pressure or heart rate as monitored by the system is not outside of the normal threshold limits (hypotensive or hypertensive, bradycardic or tachycardic), or if the controller output (after it has timed out) has resulted in a correction of the blood pressure or heart rate to within a predetermined threshold range, no further electrical signal is applied to the target site and the controller continues to monitor the patient via the sensors. A block diagram of an algorithm which may be used in the present invention is shown in FIG. 3.

Figure 3:
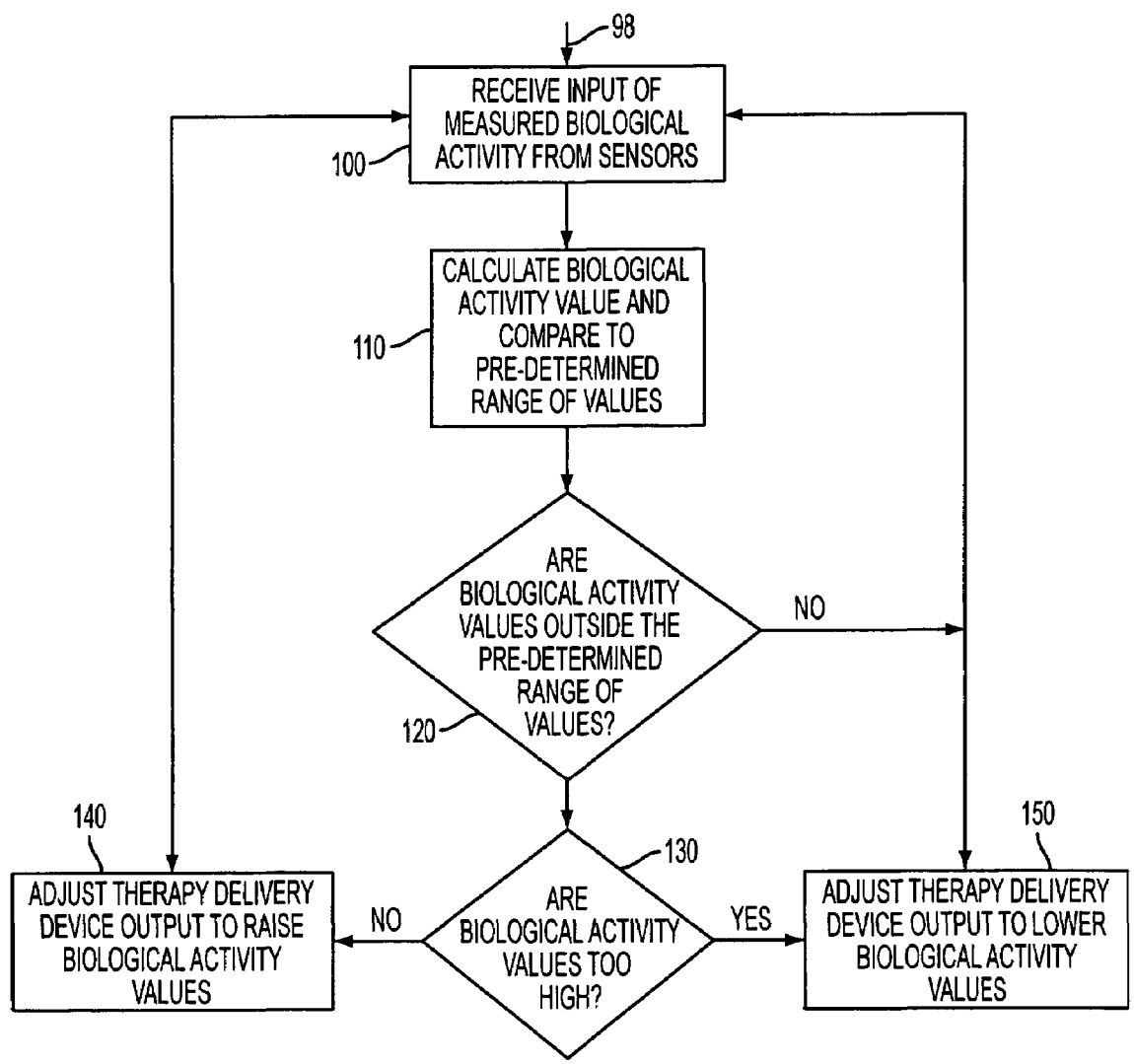
FIG. 3 is a block diagram of an algorithm to determine action which may be taken by the controller microprocessor in response to sensor input.

Referring to FIG. 3, suitably conditioned and converted sensor data 98 is input to the algorithm in block 100. The program computes at least one value of at least one biological activity related to a particular medical condition such as, for example, blood pressure, heart rate, or cardiac output, and compares the measured value of the biological activity to a pre-determined range of values, which is determined in advance to be the desired therapeutic range of values. This range is programmed into the microprocessor via the telemetry or communications port of the controller. The algorithm compares, 110, and then determines whether or not the measured value lies outside the predetermined range of values, 120. If the measured biological activity value is not outside the predetermined range of values, the program continues to monitor the sensors and reiterates the comparison part of the algorithm. If the measured biological value is outside of the pre-determined range of values, a determination or comparison is made, 130, as to whether the value is too high or too low compared with the pre-determined range. If the biological activity value is too high, an adjustment to the therapeutic delivery device is made, 150, to lower the biological activity value of the patient by calculating an output signal for pulse generator or drug delivery device to deliver a sufficient amount of the pharmaceutical or electrical stimulation to lower the biological activity of the patient. The algorithm continues to monitor the biological activity following the adjustment. If the biological activity value is too low then an adjustment to the therapeutic delivery device is made, 140, to raise the biological activity value by calculating an output signal for the pulse generator or drug delivery device to deliver a sufficient amount of a pharmaceutical or electrical stimulation to raise the biological activity value of the patient. The algorithm continues to monitor the biological activity of the patient, 100, following the adjustment. The amount of adjustment made may be determined by proportional integral derivative algorithms of by implementation of Fuzzy logic rules.

With respect to the control of specific electrical parameters, the stimulus pulse frequency may be controlled by programming a value to a programmable frequency generator using the bus of the controller. The programmable frequency generator provides an interrupt signal to the microprocessor through an interrupt line when each stimulus pulse is to be generated. The frequency generator may be implemented by model CDP 1878 sold by Harris Corporation. The amplitude for each stimulus pulse may be programmed to a digital to analog converter using the controller's bus. The analog output is conveyed through a conductor to an output driver circuit to control stimulus amplitude. The microprocessor of the controller may also program a pulse width control module using the bus. The pulse width control provides an enabling pulse of duration equal to the pulse width via a conductor. Pulses with the selected characteristics are then delivered from signal generator through a cable and lead to the target site or to a device such as a proportional valve or pump. The microprocessor executes an algorithm to provide stimulation with closed loop feedback control as shown in U.S. Pat. No. 5,792,186 which is incorporated herein by reference in its entirety. For some types of sensors, a microprocessor and analog to digital converter will not be necessary. The output from sensor can be filtered by an appropriate electronic filter in order to provide a control signal for signal generator. An example of such a filter is found in U.S. Pat. No. 5,259,387 "Muscle Artifact Filter, Issued to Victor de Pinto on Nov. 9, 1993, incorporated herein by reference in its entirety.

At the time the therapy delivery device is implanted, the clinician programs certain key parameters into the memory of the implanted device via telemetry. These parameters may be updated subsequently as needed. The clinician may also program the the range of values for pulse width, amplitude and frequency which the therapy delivery device may use to optimize the therapy. The clinician may also choose the order in which the parameter changes are made. Alternatively, the clinician may elect to use default values or the microprocessor may be programmed to use fuzzy logic rules and algorithms to determine output from the therapeutic delivery device to the patient based on sensor data and threshold values for the biological activity.

Although the application of sensors to detect bodily activity are part of embodiments of systems of the present invention, the present invention also contemplates the relevant bodily activity to be detected without sensors. In such case, the neuromodulation parameters are adjusted manually in response to the clinical course of the disease or reporting by the patient.

The present invention also provides a method for enhancing memory, learning, and/or cognitive capacity in a normal individual comprising placing a therapy delivery device on a target site of a cerebello-thalamo-cortical pathway and/or the cortical-ponto-cerebellar pathway and activating the therapy delivery device to deliver therapy to the target site to enhance the memory, learning, and/or cognitive capacity.

Neuromodulation of the target sites of the present invention can be temporary or short term, such as less than 10 days, intermediate (10-30 days) or chronic (greater than 30 days).

Although not wishing to be bound by the description of a particular procedure, one exemplary procedure effectuating the methods of the present invention shall now be described with respect to electrical stimulation of a deep cerebellar target site. Generally, the procedure begins with the patient having a stereotactic head frame mounted to the patient's skull, although frameless techniques may also be used. The patient then typically undergoes a series of MRI and/or CT sessions, during which a series of two dimensional slice images of the patient's brain are built up into a quasi-three dimensional map in virtual space. This map is then correlated to the three dimensional stereotactic frame of reference in the actual surgical field. In order to align these two coordinate frames, both the instruments and the patient should be situated in correspondence to the virtual map. A current method of achieving this alignment is to rigidly mount to the head frame to the surgical table. Subsequently, a series of reference points are established relative to aspects of the frame and patient's skull, so that a computer can adjust and calculate the correlation between the actual surgical field of the patient's head and the virtual space model of the patient's brain MRI scans. Initial anatomical localization of the target site is achieved either directly using the MRI images, or indirectly using interactive anatomical atlas programs that map the atlas image onto the stereotactic image of the brain. This indirect targeting approach involves entering the stereotactic anterior commissure (AC) and posterior commissure (PC) coordinates into a computer with a commercially available program containing digitized diagrams of sagittal brain sections from a standardized brain atlas. The program transcribes the patient's calculated AC-PC intercommissural line onto the digitized map at the sagittal laterality of interest. On these maps, the target sites can be localized. The subsequently generated map is overlaid onto a millimeter grid ruled in stereotactic coordinates in the anteroposterior and dorsoventral scales with a corresponding diagram of the target site.

Another method of localizing the target site involves the fusion of functional and structural medical imaging. Such methods for localizing targets in the body and guiding diagnostic or therapeutic instruments toward a target region in the body have been described in U.S. Pat. No. 6,368,331, issued on Apr. 9, 2002 to Front et al., U.S. Patent Application Publication No. U.S. 2002/0032375, published Mar. 14, 2002 by Bauch et al., and U.S. Patent Application Publication No. U.S. 2002/0183607, published Dec. 5, 2002 by Bauch et al., all of which are hereby incorporated by reference in their entireties. Methods for target localization specifically within the nervous system, including the brain, have been described in U.S. Provisional Application No. 60/353,695, filed Feb. 1, 2002, by Rezai et al. which is hereby incorporated by reference in its entirety. Specifically, provided in U.S. Provisional Application No. 60/353,695 is a method of medical imaging, comprising: placing a fiducial marker proximate to an area of a body to be imaged; obtaining a first image of the area of the body using a first medical imaging technique, the first image including a first image of the fiducial marker; obtaining a second image of the area of the body using a second medical imaging technique, the second image including a second image of the fiducial marker, the second medical imaging technique being different than the first medical imaging technique; superimposing the first image of the area of the body and the second image of the area of the body; and aligning the first image of the first fiducial marker with the second image of the fiducial marker. Useful medical imaging techniques to obtain functional images include but are not limited to functional MRI, PET or MEG. Useful medical imaging techniques to obtain structural images include but are not limited to volumetric MRI and CT.

Subsequent to the stereotactic imaging (or functional and structural imaging), acquisition of the images, and anatomical localization, the patient is taken to the operating room. The surgery can be performed under either local or general anesthetic, Physiological localization using single-cell microelectrode recording can performed for definitively identifying the target site by neuronal firing patterns of individual neurons. Once the final target site has been identified in the actual spatial frame of reference, the electrode is inserted into the target site and a hand-held pulse generator (Screener) is used for intraoperative test stimulation. Various pole combinations and stimulation frequency, pulse width, and intensity are used to determine the thresholds for therapeutic and adverse effects. Thereafter the electrode is locked into a burr hold ring, for example, to prevent lead migration. The proximal portion of the electrode is then attached to a transcutaneous pacing wire for a test trial period. After the test period, the patient may undergo implantation of a pulse generator or radio-frequency-coupled receiver.

If an implantable pulse generator is to be used, such implantation is generally carried out with the patient under general anesthesia. The pulse generator is implanted in the infraclavicular space by tunneling from the frontal inicision to the infraclavicular space. The pulse generator can be powered by a battery and can be activated externally by an external transmitter.

Of course, the above-mentioned procedure is only exemplary and stimulation of target sites according to the present invention is not limited to any particular procedure. Further, the foregoing description has been set forth merely to illustrate the invention and are not intended as being limiting.

Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. For example, although methods of treating specific medical conditions are described, target sites can be stimulated to treat medical conditions related to the skeletal system, the immunological system, the vascular/hematological system, the muscular/connective tissue system, the neurological system, the visual system, the auditory and vestibular system, the dermatological system, the endocrine system, the olfactory system, the cardiovascular system, the genitourinary system, the gastrointestinal system, the respiratory system, as well as treating mass lesions such as abscesses, tumors, and aneurysms. Furthermore, all references cited herein are incorporated by reference in their entirety.

We claim:

1. A method of treating a medical condition resulting from a stroke or a traumatic etiology comprising: placing a therapy delivery device on a target site, the target site selected from the group consisting of at least one of a deep cerebellar target site; a thalamic nucleus target site that is within the cerebello-thalamo-cortical pathway, the thalamic nucleus target site including a projection from a deep cerebellar nucleus and including a projection to the cerebral cortex; and projections from the cerebellum to the thalamus; and activating the therapy delivery device to deliver a therapy signal to the target site to treat the medical condition resulting from the stroke or the traumatic etiology.

2. The method of claim 1, wherein the medical condition results from the stroke.

3. The method of claim 1, wherein the medical condition results from the traumatic etiology.

4. The method of claim 1, wherein the target site is the deep cerebellar target site.

5. The method of claim 1, wherein activating the therapy delivery device comprises initiating delivery of a therapy signal to the target site and adjusting parameters of the therapy signal to treat the medical condition resulting from the stroke or the traumatic etiology.

6. The method of claim 1, wherein the target site is a thalamic nucleus target site that is within the cerebello-thalamo-cortical pathway, the thalamic nucleus target site including a projection from a deep cerebellar nucleus and including a projection to the cerebral cortex.

7. The method of claim 1, wherein the target site is a projection from the cerebellum to the thalamus.

* * * * *

UNITED STATES PATENT AND TRADEMARK OFFICE
CERTIFICATE OF CORRECTION

PATENT NO. : 7,640,063 B2
APPLICATION NO. : 11/121005
DATED : December 29, 2009
INVENTOR(S) : Machado et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 615 days.

Signed and Sealed this

Ninth Day of November, 2010

David J. Kappos
*Director of the United States Patent and Trademark Office*